| United States Patent [19] | [11] 3,932,499 |
| Adams et al. | [45] Jan. 13, 1976 |

[54] 2-(SUBSTITUTED BIPHENYLYL) PROPIONIC ACIDS

[75] Inventors: Stewart Sanders Adams; Bernard John Armitage; John Stuart Nicholson, all of Nottingham, England

[73] Assignee: The Boots Company Limited, Nottingham, England

[22] Filed: Sept. 22, 1971

[21] Appl. No.: 182,857

[30] Foreign Application Priority Data
Oct. 12, 1970  United Kingdom............... 48405/70

[52] U.S. Cl. ...... 260/515 A; 260/247.1; 260/307 F; 260/465 D; 260/485 F; 260/469; 260/558 S; 260/558 D; 260/558 R; 260/501.16; 260/520; 260/578; 260/592; 260/599; 424/308; 424/316; 424/317

[51] Int. Cl.$^2$......................................... C07C 63/52
[58] Field of Search............ 260/515 A, 469, 501.16

[56] References Cited
UNITED STATES PATENTS
3,624,142  11/1971  Shen et al............................ 260/515
3,755,427  8/1973  Adams et al........................ 260/515

FOREIGN PATENTS OR APPLICATIONS
56/65  2/1965  Ireland

Primary Examiner—James A. Patten
Attorney, Agent, or Firm—Lawrence Rosen; E. Janet Berry

[57] ABSTRACT

2-(Substituted biphenylyl)propionic acids and salts and esters thereof, said substituents being selected from fluorine and bromine atoms, useful as anti-inflammatory agents, and their preparation.

9 Claims, No Drawings

2-(SUBSTITUTED BIPHENYLYL) PROPIONIC ACIDS

This invention relates to novel 2-(substituted biphenylyl)propionic acids, lower alkyl esters thereof and salts thereof, which have been found to possess valuable biological properties.

According to one feature of the invention there are provided compounds of general formula I

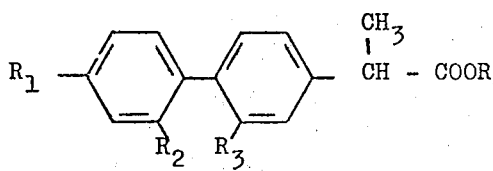

... I in which
R$_1$ is fluorine or bromine;
one of R$_2$ and R$_3$ is fluorine or bromine and the other is hydrogen; and R is hydrogen or lower alkyl;
together with pharmaceutically acceptable inorganic and organic salts of said compounds when R is hydrogen.

Typical methods suitable for the preparation of the compounds of general formula I are as follows. Processes for the preparation of the stated starting materials and exact reaction conditions for the typical methods for the preparation of compounds of general formula I will be readily apparent to those skilled in the art from inherent knowledge, the prior art literature and the examples appended to this specification. As the methods are so-called "analogy processes" the descriptions have been kept brief and it is to be understood that any known procedures may be used to carry out the methods in addition to those procedures to which specific references be made.

In the following description of the preparation of Acids and Esters
R$_o$ represents

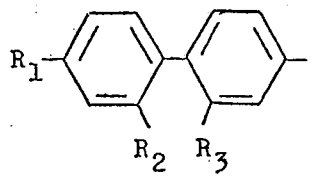

Acids
1. Hydrolysis of

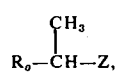

wherein Z is cyano, carbamoyl, N,N-disubstituted thiocarbamoyl, or COOR$_4$ in which R$_4$ is an ester-forming group, especially lower alkyl. The N,N-disubstituted thiocarbamoyl group is preferably derived from morpholine.

The hydrolysis may be carried out according to methods well-known in the art, for example by the use of acid or alkali in water, in an organic liquid reaction medium, or in a mixture thereof; a treatment temperature of 15°–150°C. is convenient. Preferably the hydrolysis is carried out by refluxing in the presence of an alkali metal hydroxide or of a mineral acid, and the organic liquid reaction medium is a lower alkanol.

The starting materials may be prepared, for example, from the substituted acetophenones R$_o$—CO—CH$_3$ by conventional means; other methods include the methods outlined below under the "Esters" heading.

2. Decarboxylation of

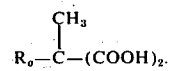

This may be carried out by heating the compound at about 200°C.

The starting materials may be conveniently prepared in conventional manner, for example by reacting an alkyl ester of an acid R$_o$—CH$_2$—COOH with an alkyl carbonate and an alkali metal alkoxide to yield an alkali metal derivative of a compound of formula R$_o$—CH—(COOalkyl)$_2$, methylating this and hydrolysing the product.

3. Methylation of R$_o$—CH$_2$—COOH.

A metal (e.g. sodio) derivative of the acetic acid is used, prepared for example by reaction of the acid with an alkali metal amide (e.g. sodamide) in a suitable medium e.g. liquid ammonia. Conventional methylating agents may be used e.g. methyl iodide, dimethyl sulphate, and the like.

4. Oxidation of

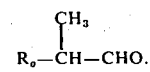

The oxidation may be carried out using any suitable oxidising agent such as permanganates, chromic acid, dichromates, per acids, hydrogen peroxide, nitric acid, hypochlorites, silver oxide, or oxygen. A very convenient procedure involves oxidation in aqueous ethanol with alkali (e.g. an alkali metal hydroxide) and silver oxide.

The starting materials may be prepared by the methods described for related compounds in our British Pat. Specification No. 1,160,725.

5. Reduction cleavage of

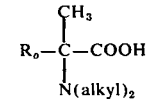

This may be achieved by conventional methods such as by catalytic hydrogenation e.g. using a palladium charcoal catalyst, or by treatment with sodium in liquid ammonia.

The starting materials may be prepared by the methods described for related compounds in our British Pat. Specification No. 1,167,192.

6. Hydrogenation of

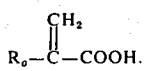

Typical procedures include hydrogenation over a conventional catalyst such as, for example, palladium, palladium oxide or platinum in an inert solvent such as a lower alkanol, benzene, toluene, xylene, tetrahydrofuran, dioxan and acetic acid, at a temperature of about 0°C. up to the reflux temperature of the system.

The starting materials may be prepared conventionally such as for example, by the following reaction scheme:

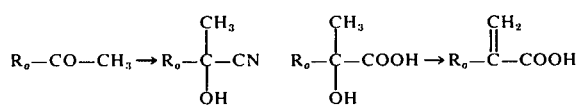

7. The reaction

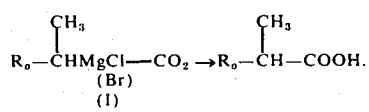

The Grignard reagent may be prepared conventionally by reaction of the appropriately substituted alkyl halide with magnesium in the presence of ether; it is then treated in ethereal solution with carbon dioxide and the additive compound so formed is decomposed with acid e.g. dilute sulphuric acid.

8. By means of the Ullmann reaction: i.e.

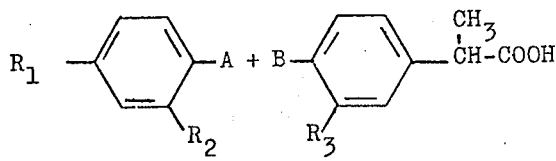

wherein A is iodine when $R_1$ and/or $R_2$ are/is bromine, and A is iodine or bromine when $R_1$ is fluorine and $R_2$ is hydrogen or fluorine; and B is iodine when $R_3$ is bromine and B is iodine or bromine when $R_3$ is hydrogen or fluorine. This reaction is normally carried out by heating the compounds together at 100°–350°C. in the presence of a metal catalyst especially copper powder or copper bronze.

9. Hydrolysis of

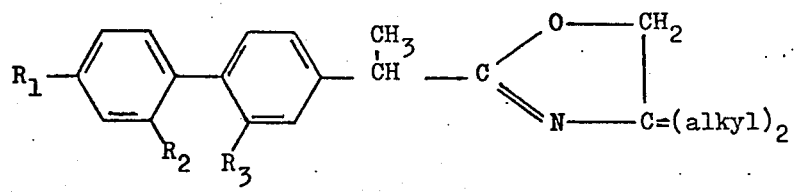

wherein "alkyl" is preferably methyl. Typical hydrolysis conditions are described under method (1); acid hydrolysis is preferred.

The starting materials may be prepared by the reaction:

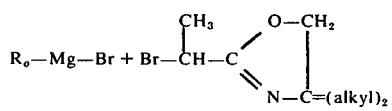

10. Removal of sulphur dioxide from a compound of formula

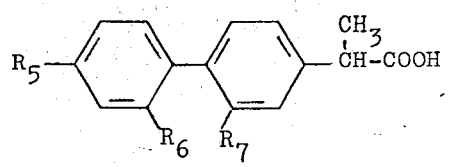

in which at least one of the symbols $R_5$, $R_6$ and $R_7$ is a fluorosulphonyl or bromosulphonyl group and the remaining symbols correspond to the desired values of $R_1$, $R_2$ and $R_3$, by heating in the presence of a compound useful in decomposing sulphonyl fluorides and bromides. Typical compounds are nickel, platinum, palladium, ruthenium, tris(triphenylphosphine)rhodium chloride, tris(triphenylphosphine(ruthenium dichloride, tetra(triphenylphosphine)-ruthenium dichloride and tris(triphenylphosphine)rhodium fluoride. A temperature of 100°–300°C. is generally used. The reaction may be carried out in the presence of an inert organic solvent, such as benzene or xylene, although the use of a solvent is not necessary.

11. Reaction of a compound of formula

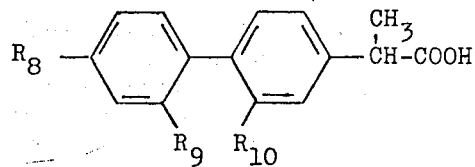

in which at least one of the symbols $R_8$ $R_9$ and $R_{10}$ is an amino group and the other symbols correspond to the desired values of $R_1$, $R_2$ or $R_3$ is known manner so as to convert said amino group to the desired halogen atom. Examples of known procedures include the Sandmeyer reaction, wherein the amino compound is diazotised and reacted with a cuprous halide, and the Schiemann reaction wherein the amino compound is diazotised in the presence of a fluorinating agent to form a fluorodiazonium derivative which is then decomposed by heating to give the corresponding fluoro compound. Suitable fluorinating agents include hydrogen fluoride, fluoboric acid, fluosilicic acid and phosphorus pentafluoride.

Esters

1. Esterification of the acids by conventional means:

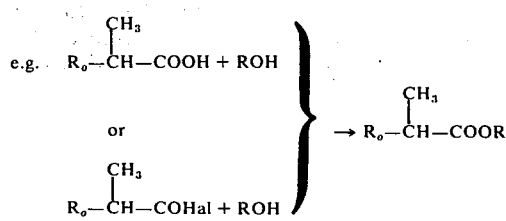

2. Alcoholysis of

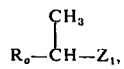

wherein $Z_1$ is cyano, carbamoyl, or N,N-disubstituted thiocarbamoyl (e.g. derived from morpholine).

3. By means of methods (3), (6), (8), (10) and (11) as described under "Acids" but starting with the desired ester in place of the acid.

4. By alcoholysis of the oxazolines described under "Acids (9)".

Salts

1. Reaction of the acids with organic or inorganic bases.

2. Alkaline hydrolysis of

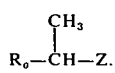

The compounds of general formula i possess anti-inflammatory activity and are useful for the treatment of diverse inflammatory conditions. They also possess analgesic and antipyretic properties and are useful for the treatment of conditions of pain and pyretic conditions. They are useful for the treatment of these three conditions individually or in any combination. A particularly notable and important feature of the compounds is their long lasting effect. This feature allows a relatively high blood level to be achieved for a long period following a single dose (in some cases 24 hours or longer), in contrast to short acting compounds e.g. 2-(4-isobutylphenyl)propionic acid where there is no substantial amount of compound in the blood only a short time following a single dose, e.g. after 3–6 hours in the case of 2-(4-isobutylphenyl)propionic acid. Thus the compounds of the invention need only be administered once, or sometimes twice, per day, whereas the short acting compounds require to be administered at least three times, and often four times, per day.

The activity of the compounds of the invention has been determined in experimental animals using pharmacological tests which are known to be capable of characterising compounds possessing anti-inflammatory activity, and also analgesic and antipyretic activity; long lasting effect has been confirmed by blood level and other experiments.

Preferred compounds of the invention are those wherein R is hydrogen. It is believed that when salts and esters derived from these acids are used in place of the acids said derivatives are metabolised by the animal body and are converted in the body into the corresponding acids.

It will be appreciated that, since the compounds of general formula I possess an asymmetric carbon atom, they are ordinarily present in the form of a racemic mixture. The resolution of such racemates may be carried out by any conventional method and the separated optically active stereo-isomers form part of the present invention.

The compounds of the invention may be administered in the conventional manner of other anti-inflammatory, analgesic, and antipyretic agents, for example orally, topically, rectally or parenterally, preferably orally. The optimum dosage rate varies with the route of administration, but normally lies within the range 0.07–3.5 mg./kg./day. For oral administration the dosage rate is preferably 5–250 mg. per subject per day, optionally in divided doses; and the unit dose may vary from 2.5 mg. to 250 mg. per subject.

In use, the compounds of the invention are administered in conventional formulations and accordingly the invention also provides therapeutic compositions which comprise a compound of the invention in association with pharmaceutical excipients for the production of compositions for oral, topical, rectal or parenteral administration. These compositions preferably contain 0.1–90% by weight of a compound of the invention.

Preferred compositions of the invention are compositions for oral administration, and these are the conventional pharmaceutical forms for such administration, such as for example tablets, capsules, lozenges, powders, effervescent granules, syrups and aqueous and oily suspensions. The excipients used in the preparation of these compositions are the excipients of the pharmacist's art. Thus is the preparation of tablets, typical excipients include disintegrating agents, e.g., maize starch and lubricating agents, e.g. magnesium stearate; in the preparation of the capsules, standard gelatin capsules may be used containing the active ingredient alone or admixed with a diluent. The liquid compositions may comprise as excipients water and sucrose to provide syrups, water, dispersing agents and suspending agents, e.g., sodium carboxymethylcellulose to provide aqueous suspensions, and a non-toxic oil, e.g., a vegetable oil such as arachis oil and a suspending agent to provide oily suspensions.

Other preferred compositions of the invention are compositions for rectal administration, and these are the conventional pharmaceutical forms for such administration, such as for example suppositories with cocoa butter or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1–4 carbon atoms which may contain a small proportion of water.

Compositions for parenteral administration are the conventional pharmaceutical forms for such administration, for example sterile suspensions in aqueous or oily media or sterile solutions in propylene glycol.

In some formulations it may be beneficial to use the compounds of the invention in the form of particles of very small size, such as for example, as obtained by fluid energy milling, e.g., micronizing.

The invention further provides a method of treating inflammatory conditions, conditions of pain and pyretic conditions, individually or in any combination, which comprises administering a compound of the invention, preferably orally.

The products of the present invention may of course be employed in combination with other active anti-inflammatory agents, analgesics, and antipyretic agents, or with other drugs, as is already conventional in the art for other existing anti-inflammatory, analgesic and antipyretic materials.

The following non-limitative examples illustrate the invention.

EXAMPLE 1

Ethyl 2-(2′, 4′-difluoro-4-biphenylyl)-2-methylmalonate (5.42 g.) was refluxed for 2 hours with a mixture of 2.5N aqueous sodium hydroxide (27 ml.) and ethanol (13.5 ml.). The solution was then evaporated to a small bulk; the solid sodium salt was dissolved in water and the solution acidified with dilute hydrochloric acid. The resulting precipitate of crude 2-(2′,4′-difluoro-4-biphenylyl)-2-methylmalonic acid was decarboxylated by heating for 20 minutes at 200°C. The product was purified by preparative layer chromatography using 5% acetic acid/petroleum ether b.p. 60°–80°C. and eluting with ethyl acetate; recrystallisation from petroleum ether b.p. 80°–100°C. gave 2-(2′,4′-difluoro-4-biphenylyl)propionic acid, m.p. 125°–127°C.

The starting material was prepared as follows. 2,4-Difluoroaniline and butyl nitrite were reacted with benzene in a modified Gomberg reaction to give 2,4-difluorobiphenyl, m.p. 63°–65°C. which was reacted with acetyl chloride in a Friedel-Crafts reaction to give 4-acetyl-2′,4′-difluorobiphenyl, m.p. 82.5°–83.5°C. This was subjected to the Willgerodt reaction using morpholine and sulphur, followed by hydrolysis, to give 2′,4′-difluoro-4-biphenylylacetic acid, m.p. 143°–145°C., which was esterified to give ethyl 2′,4′-difluoro-4-biphenylylacetate, b.p. 129°–130°C./0.2 mm. This ester was treated conventionally with diethyl carbonate, and then with dimethyl sulphate, to yield the required ethyl 2-(2′,4′-difluoro-4-biphenylyl)-2-methylmalonate, b.p. 172°–175°C./0.5 mm.

EXAMPLE 2

By procedures similar to those described in Example 1, ethyl 2-(2,4′-difluoro-4-biphenylyl)-2-methylmalonate was hydrolysed and the resulting crude 2-(2,4′-difluoro-4-biphenylyl)-2-methylmalonic acid was decarboxylated to give 2-(2,4′-difluoro-4-biphenylyl)propionic acid, m.p. 118°–119°C.

The starting material was prepared as follows. An Ullmann reaction using p-fluoroiodobenzene and 4-bromo-3-nitroacetophenone gave 4-acetyl-4′-fluoro-2-nitrobiphenyl, m.p. 88°–90°C., which was reduced with stannous chloride/hydrochloric acid to give 4-acetyl-2-amino-4′-fluorobiphenyl, m.p. 88°–91°C. This was subjected to the Schiemann reaction to give 4-acetyl-2,4′-difluorobiphenyl, m.p. 80°–82.5°C., which was subjected to the Willgerodt reaction using morpholine and sulphur, followed by hydrolysis, to give 2,4′-difluoro-4-biphenylylacetic acid, m.p. 144°–146°C. This was esterified to give the ethyl ester, b.p. 142°–146°C./0.35 mm., which was treated conventionally with diethyl carbonate, and then with dimethyl sulphate, to yield the required ethyl 2-(2,4′-difluoro-4-biphenylyl)-2-methylmalonate, b.p. 164°–166°C./0.05 mm.

EXAMPLE 3

2-(2′,4′-Difluoro-4-biphenylyl)propionic acid (2 g.), methanol (20 ml.) and concentrated sulphuric acid (0.6 ml.) were refluxed for 16 hours. Excess methanol was distilled in vacuo, the residue was diluted with water and the oil isolated in ether. Distillation gave methyl 2-(2′,4′-difluoro-4-biphenylyl)propionate, b.p. 118°–120°C./0.2 mm.

EXAMPLE 4

2-(2′,4′-Difluoro-4-biphenylyl)propionic acid (0.5 g.) in ether (25 ml.) was mixed with benzylamine (0.204 g.) in ether (5 ml.). The resulting precipitate was collected, washed with water and dried in vacuo to give benzylamine 2-(2′,4′-difluoro-4-biphenylyl)propionate, m.p. 148°–150°C.

EXAMPLE 5

2-(2′,4′-Difluoro-4-biphenylyl)propionic acid (7.2 g.), cinchonidine (8.1 g.) and methanol (140 ml.) were stirred for 1 hour and then evaporated to dryness. The resulting solid was recrystallised from acetone 7 times; the resulting cinchonidine salt was suspended in water, acidified with dilute sulphuric acid and the liberated free acid was isolated in ether. The ether solution was evaporated to dryness, the residue triturated with petroleum ether b.p. 60°–80°C. and the resulting solid dried in vacuo to give (+)-2-(2′,4′-difluoro-4-biphenylyl) propionic acid, m.p. 110.5–113°C., $[\alpha]_D^{20}$ + 36.3° (c, 1.625 ethanol).

EXAMPLE 6

2-(2,4′-Difluoro-4-biphenylyl)propionic acid (830 mg.), ethanol (10 ml.) and concentrated sulphuric acid (0.5 ml.) were refluxed for 16 hours. The solution was diluted with ice-water (200 ml.) and extracted with ether. After the usual washing, evaporation of the ether and distillation of the residue gave ethyl 2-(2,4′-difluoro-4-biphenylyl)-propionate, b.p. 145°–146°C./0.8 mm.

EXAMPLE 7

No. 5 hard gelatin capsules were prepared each containing the following:

| | | |
|---|---|---|
| (a) | 2-(2′,4′-difluoro-4-biphenylyl)propionic acid | 5 mg. |
| | lactose | 95 mg. |
| (b) | 2-(2′,4′-difluoro-4-biphenylyl)propionic acid | 5 mg. |
| | calcium phosphate | 5 mg. |
| | maize starch | 90 mg. |
| (c) | 2-(2′,4′-difluoro-4-biphenylyl)propionic acid | 5 mg. |
| | maize starch ⎫ | |
| | lactose ⎬ equal parts by weight | 95 mg. |
| | calcium phosphate ⎭ | |

EXAMPLE 8

The following mixture (parts by weight) was formed into tablets in conventional manner, each tablet containing 5 mg. of active ingredient:

| | |
|---|---|
| 2-(2′,4′-difluoro-4-biphenylyl)propionic acid | 5 |
| maize starch | 30 |
| lactose | 163 |
| stearic acid | 1 |
| magnesium stearate | 1 |

Compositions similar to those described in Examples 7 and 8 were prepared containing as active ingredient other compounds of the invention described in Examples 2 – 6 and 9 – 15.

EXAMPLE 9

Silver nitrate (6.8 g.) in water (8 ml.) was stirred and treated dropwise with a mixture of 13.2 N potassium hydroxide (3.04 ml.) and water (7.3 ml.). The resulting slurry was diluted with ethanol (9 ml.) and a solution of 2-(2-bromo-4'-fluoro-4-biphenylyl)propionaldehyde (5.9 g.) in ethanol (17 ml.) was added slowly. After stirring for 15 minutes, a mixture of 13.2 N potassium hydroxide (1.8 ml.) and water (1.8 ml.) was added over 1 hour, the temperature being maintained at 43°–45°C. The reaction product was then stirred at 40°C. for 30 minutes, filtered, and the filtrate distilled in vacuo to remove the ethanol. The residue was acidified with dilute hydrochloric acid, the resulting oil isolated in ether, and the extract (after conventional washing) evaporated to dryness. Recrystallisation from light petroleum b.p. 80°–100°C. gave 2-(2-bromo-4'-fluoro-4-biphenylyl)propionic acid, m.p. 129°–131°C.

The starting material was prepared by the following series of reactions:
1. p-fluoroiodobenzene + 4-bromo-3-nitroacetophenone under Ullmann conditions gave 4-acetyl-4'-fluoro-2-nitrobiphenyl, m.p. 88°–90°C.;
2. reduction of this using stannous chloride gave 4-acetyl-2-amino-4'-fluorobiphenyl, m.p. 88°–91°C.;
3. conversion of this by a Sandmeyer reaction gave 4-acetyl-2-bromo-4'-fluorobiphenyl, b.p. 152–154°C./0.7 mm.;
4. conversion of this by a Darzens reaction gave 2-(2-bromo-4'-fluoro-4-biphenylyl)propionaldehyde, b.p. 164–166°C./0.6 mm.

EXAMPLE 10

By procedures similar to those described in Example 9, 2-(4'-bromo-2'-fluoro-4-biphenylyl)propionaldehyde was oxidised to give 2-(4'-bromo-2'-fluoro-4-biphenylyl)propionic acid, m.p. 137°–139° C. (ex petroleum ether b.p. 80° – 100°C.).

The starting material was prepared by the following series of reactions:
1. 2-amino-4-bromobiphenyl was converted by a Schiemann reaction to 4-bromo-2-fluorobiphenyl, b.p. 106°–109°C./0.6 mm;
2. conversion of this by a Friedel-Crafts reaction gave 4-acetyl-4'-bromo-2'-fluorobiphenyl, m.p. 94.5–95.5°C.;
3. conversion of this by a Darzens reaction gave 2-(4'-bromo-2'-fluoro-4-biphenylyl)propionaldehyde, which was used without isolation and purification.

EXAMPLE 11

By procedures similar to those described in Example 9, 2-(2'-bromo-4'-fluoro-4-biphenylyl)propionaldehyde was oxidised to give 2-(2'-bromo-4'-fluoro-4-biphenylyl)propionic acid, m.p. 77°–79° C.

The starting material was prepared by the following series of reactions:
1. reduction of 4-fluoro-2-nitrobiphenyl using stannous chloride gave 2-amino-4-fluoro-biphenyl, b.p. 106°–107° C/0.6 mm.;
2. conversion of this by a Schiemann reaction gave 2-bromo-4-fluorobiphenyl, b.p. 104°C/0.8 mm.;
3. conversion of this by a Friedel-Crafts reaction gave 4-acetyl-2'-bromo-4'-fluorobiphenyl, m.p. 70°–72°C.;
4. conversion of this by a Darzens reaction gave 2-(2'-bromo-4'-fluoro-4-biphenylyl)propionaldehyde which was used without isolation and purification.

EXAMPLE 12

By procedures similar to those described in Example 9, 2-(4'-bromo-2-fluoro-4-biphenylyl)propionaldehyde was oxidised to give 2-(4'-bromo-2-fluoro-4-biphenylyl)propionic acid, m.p. 133°–135°C.

The starting material was prepared by the following series of reactions:
1. p-bromoiodobenzene + 4-bromo-3-nitroacetophenone under Ullmann conditions gave 4-acetyl-4'-bromo-2-nitrobiphenyl, m.p. 118°–118.5°C.;
2. reduction of this using stannous chloride gave 4-acetyl-2-amino-4'-bromobiphenyl, m.p. 159°–160°C.;
3. conversion of this by a Sandmeyer reaction gave 4-acetyl-2,4'-dibromobiphenyl, m.p. 82.5°–84.5°C.;
4. conversion of this by a Darzens reaction gave 2-(4'-bromo-2-fluoro-4-biphenylyl)propionaldehyde, which was used without isolation and purification.

EXAMPLE 13

By procedures similar to those described in Example 9, 2-(4'-bromo-2-fluoro-4-biphenylyl)propionaldehyde was oxidised to give 2-(4'-bromo-2-fluoro-4-biphenylyl)propionic acid, m.p. 139°–140°C.

The starting material was prepared by the following series of reactions:
1. 4-acetyl-2-amino-4'-bromobiphenyl (see Example 12) was converted by a Schiemann reaction to give 4-acetyl-4'-bromo-2-fluorobiphenyl, m.p. 89–91°C.;
2. conversion of this by a Darzens reaction gave 2-(4'-bromo-2-fluoro-4-biphenylyl)propionaldehyde, which was used without isolation and purification.

EXAMPLE 14

By procedures similar to those described in Example 9, 2-(2',4'-dibromo-4-biphenylyl)propionaldehyde was oxidised to give 2-(2',4'-dibromo-4-biphenylyl)propionic acid, m.p. 114°–116°C.

The starting material was prepared by the following series of reactions:
1. 2,4-dibromobiphenyl was converted by a Friedel-Crafts reaction to 4-acetyl-2',4'-dibromobiphenyl, m.p. 99°–101°C.;
2. this was converted by a Darzens reaction to give 2-(2',4'-dibromo-4-biphenylyl)propionaldehyde, which was used without isolation and purification.

EXAMPLE 15

2-(2',4'-Difluoro-4-biphenylyl)propionic acid (1.3 g.) in acetone (5 ml.) was treated with a solution of sodium hydroxide (0.2 g.) in water (1 ml.). An immediate precipitate of the sodium salt was formed. After dilution with acetone (5 ml.) the solid was collected, washed with acetone (5 ml.), dried in vacuo and recrystallised from water (10 ml.) to give sodium 2-(2',4'-difluoro-4-biphenylyl)propionate, m.p. 213°–215°C. (in the form of a dihydrate).

We claim:
1. A compound of formula I

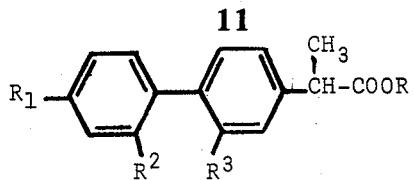

in which
R₁ is fluorine or bromine;
one of R₂ and R₃ is fluorine or bromine and the other is hydrogen;
and R is hydrogen or lower alkyl; (together with) or a pharmaceutically acceptable inorganic and organic salt(s) of said compound(s) when R is hydrogen.

2. 2-(2',4'-Difluoro-4-biphenylyl)propionic acid.
3. 2-(2'-Bromo-4'-fluoro-4-biphenylyl)propionic acid.
4. 2-(2,4'-Difluoro-4-biphenylyl)propionic acid.
5. 2-(2-Bromo-4'-fluoro-4-biphenylyl)propionic acid.
6. 2-(2',4'-Dibromo-4-biphenylyl)propionic acid.
7. 2-(4'-Bromo-2'-fluoro-4-biphenylyl)propionic acid.
8. 2-(4'-Bromo-2-fluoro-4-biphenylyl)propionic acid.
9. 2-(2,4'-Dibromo-4-biphenylyl)propionic acid.

* * * * *